(12) United States Patent
Bresina et al.

(10) Patent No.: US 6,395,035 B2
(45) Date of Patent: May 28, 2002

(54) STRAIN REGULATING FUSION CAGE FOR SPINAL FUSION SURGERY

(75) Inventors: Stephen J. Bresina, Davos; Konrad Tagwerker, Basel; Manuel Schaer, Muttenz, all of (CH)

(73) Assignee: Synthes (U.S.A.), Paoli, PA (US)

( * ) Notice: Subject to any disclaimer, the term of this patent is extended or adjusted under 35 U.S.C. 154(b) by 0 days.

(21) Appl. No.: 09/829,995

(22) Filed: Apr. 11, 2001

Related U.S. Application Data

(63) Continuation of application No. PCT/EP98/06621, filed on Oct. 20, 1998.

(51) Int. Cl.$^7$ .................................................. A61F 2/44
(52) U.S. Cl. ................................ 623/17.15; 623/17.11; 606/61
(58) Field of Search ..................... 623/17.16, 17.11, 623/17.13, 17.15, 17.14, 16.11, 18.11; 606/61, 71, 73, 74, 75

(56) References Cited

U.S. PATENT DOCUMENTS

| | | | |
|---|---|---|---|
| 5,320,644 A | 6/1994 | Baumgartner | 623/17 |
| 5,423,817 A | 6/1995 | Lin | 606/61 |
| 5,458,638 A | * 10/1995 | Kuslich et al. | 623/17.16 |
| 5,676,702 A | 10/1997 | Ratron | 623/17 |
| 5,749,916 A | 5/1998 | Richelsoph | 623/17 |
| 5,888,227 A | 3/1999 | Cottle | 623/17 |
| 5,984,967 A | * 11/1999 | Zdeblick et al. | 623/17.16 |
| 6,129,763 A | * 10/2000 | Chauvin et al. | 623/17.15 |
| 6,136,031 A | * 10/2000 | Middleton | 623/17.16 |
| 6,143,031 A | 11/2000 | Knothe et al. | 623/17 |

FOREIGN PATENT DOCUMENTS

| | | |
|---|---|---|
| EP | 0538183 | 4/1993 |
| WO | WO 98/09586 | 9/1996 |
| WO | WO 98/14142 | 9/1997 |

* cited by examiner

*Primary Examiner*—Pedro Philogene
(74) *Attorney, Agent, or Firm*—Pennie & Edmonds LLP

(57) ABSTRACT

An intervertebral fusion cage for insertion between two adjacent, opposing vertebrae, wherein the fusion cage is constructed in a way that stress absorbed by the cage is transferred to the graft material in the hollow inner cavity, thus allowing ideal strain levels to be attained in the graft material under minimal loads, while also offering a level of protection to the graft material preventing mechanical failure of the graft material due to high strains.

24 Claims, 6 Drawing Sheets

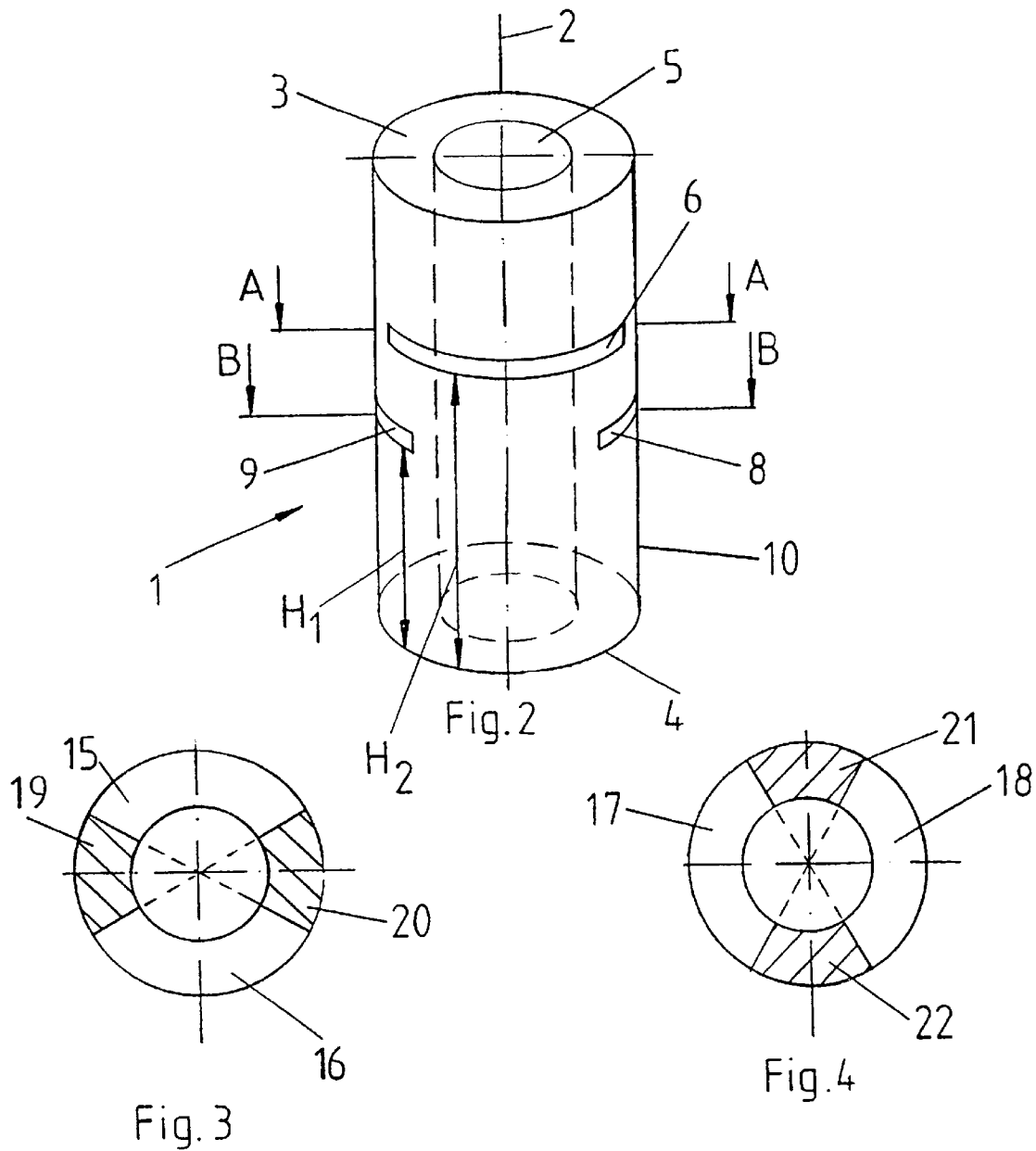

STRAIN REGULATING FUSION CAGE FOR SPINAL FUSION SURGERY

CROSS-REFERENCE TO RELATED APPLICATION

This application is a continuation of International Application No. PCT/EP98/06621, filed Oct. 20, 1998, the disclosure of which is hereby incorporated herein by express reference thereto.

FIELD OF INVENTION

This invention is directed to an intervertebral fusion cage for insertion between two adjacent, opposing vertebrae. The fusion cage is constructed in a way that stress absorbed by the cage is transferred to the graft material in the hollow inner cavity, thus allowing ideal strain levels to be attained in the graft material under minimal loads, while also offering a level of protection to the graft material preventing mechanical failure of the graft material due to high strains.

BACKGROUND OF THE INVENTION

The area of spinal implants has progressed rapidly in the last decade. Recent developments have been focused on various elements of the cage type implant design. Cage type implants are typically used for spinal fusion surgeries wherein the implant is placed between two opposing vertebrae so that a collapsed disc space is reopened to help restore the curvature of the spine and to relieve pressure on the nerves and/or spinal cord. The cage acts to provide support until the graft material ossifies and fuses the two adjacent vertebral body endplates together. The sooner the ossification occurs and fusion is completed, the better for the patient.

Fusion cages, typically hollow, are usually cylindrical or rectangular in shape with an external threaded or toothed portion for gripping the vertebral end plates in order to prevent the cage from shifting. The hollow area can be filled with graft in order to promote vertebrae fusion. Fusion cages tend to allow for smaller incisions and less invasive surgery techniques.

One technique suggested in the prior art was disclosed in PCT Publication No. WO 98/09586 of Webb et al. A hollow cylindrical intervertebral implant, made essentially of a ceramic material having a maximum porosity of 30 percent by volume, with the pores filled with air, is designed to bear the different loadings onto the vertebral column. The implant provides sufficient support at its end plates to prevent these end plates from sinking into the adjacent vertebral bodies.

U.S. Pat. No. 5,888,227 of Cottle discloses another type of intervertebral implant consisting of a frame-like cage enclosing a space. The cage is substantially wedge-shaped with top and bottom surfaces diverging towards the front wall, providing the advantage that, owing to the large bone bearing area of the top and bottom surfaces, the implant is prevented from sinking into the end plates of the body of the vertebra.

This category of existing cages has the disadvantage of being stiff, despite the intricate cutout patterns, which tends to shield the graft from stress and strain.

Another intervertebral implant disclosed in U.S. Pat. No. 6,143,031 of Knothe et al. consists of a flattened shaped hollow element. The upper and lower bone-contact surfaces can be compressed elastically towards the inner chamber of the element in such a way that the maximum distance between the upper and lower bone contact surfaces can be reduced by 0.5 mm to 5.0 mm.

Cages of this type have the disadvantage that the graft introduced into the cage endures strains that are proportional to the load.

Yet another type of intervertebral implant is disclosed in U.S. Pat. No. 5,676,702 of Ratron. The disclosed prosthesis provides an elastically deformable body having a spring rate $k_1$ so that an upper aperture within the prosthesis closes under a certain load. Once this upper aperture is closed, a spring rate $k_2$, different than spring rate $k_1$, is achieved causing the adjacent vertebral bodies to endure a higher load. This known intervertebral implant does not disclose one or more cavities in the normal direction wherein graft material could be introduced to promote ossification to fuse the two adjacent vertebral body endplates together. The different spring rates allow the implant to increase in stiffness as the end of the flexion/extension range of motion is reached.

Each of the above-identified patents, as well as many other prior art documents, only partially address issues of importance in spinal implants using graft material for the purpose of stimulating new bone formation. Most are directed to an implant acting to separate two collapsed vertebral discs, but do not address the fusion of the graft material inside the cage. In addition to a constant objective to limit the size of an implant to allow for the most minimally invasive types of surgery, proper fusion of the graft material is paramount in implants created for new bone formation.

It has been found that bone remodelling is controlled by peak strain, and that just a few cycles per day of strain above a certain level, e.g., 1000 $\mu\epsilon$, is enough to maintain bone. Strains above 1000 $\mu\epsilon$ and up to 5 percent, or 50,000 $\mu\epsilon$, proportionally increase new bone formation. It would be advantageous to provide a fusion cage that allowed the graft material to be exposed to such strain levels, whereby the graft would be able to mineralize more quickly than prior art implants.

The strain $\epsilon$ is thereby defined as $\epsilon = \delta L/L$, with $\delta L$ being the deformation of the body in the direction of the axis where the load is applied and L being the height or length of the unloaded body in the direction of the axis where the load will be applied.

An additional related problem with known cage designs is that the strain applied to the graft is not identical for all patients. A small patient will load the cage less than a large patient. If a patient is experiencing pain, the load on the cage, and therefore the strain on the graft material, will be decreased as compared to a patient that is not experiencing pain.

Furthermore, a certain load threshold is required to reach the optimal strain level. Therefore, the strain applied to the graft may never be adequate for the promotion of bone formation. The known cages are stiff and the load required to produce a strain >1000 $\mu\epsilon$ can be high.

In light of the foregoing, a need exists for an improved fusion cage. The present invention is directed to a fusion cage allowing ideal strain levels to be attained in the enclosed graft material under minimal loads, while at the same time, protecting the graft from high strains that can lead to mechanical failure of the graft. The intervertebral cage is designed to be very flexible under small axial loads. Once the required strain level is reached, contact between the upper and lower portions of the cage significantly increases the stiffness of the device and, therefore, higher loads will only create small additional strain. This invention allows a relatively consistent strain to be applied to the graft material regardless of the applied physiological load.

SUMMARY OF THE INVENTION

The present invention is directed to an intervertebral fusion cage for implantation in an intervertebral space between adjacent vertebrae. The fusion cage includes: a body having a central axis, a first outer surface, and a first stiffness; a central cavity for containing graft material having a second outer surface and extending through the body coaxial to the central axis; a circumferential sidewall between the first outer surface and the second outer surface; an upper and a lower contact surface perpendicular to the central axis, wherein the upper and lower contact surfaces contact the adjacent vertebrae and have front and back sides; and a plurality of slots transverse to the central axis, each of the slots having a minimal width and extending through the circumferential sidewall.

When the body is compressed along the central axis, the slots close to their respective minimal widths providing the body a second stiffness greater than the first stiffness. In one embodiment, the plurality of slots close to their respective minimal widths under a required load resulting in a strain level of 1,000 $\mu\epsilon$ to 50,000 $\mu\epsilon$. In a more preferred embodiment, the plurality of slots close to their respective minimal widths under a required load resulting in a strain level of 3,000 $\mu\epsilon$ to 10,000 $\mu\epsilon$. The minimal widths can range from 0.018 mm to 0.15 mm and can be different from each other.

The cage can be conical, cylindrical, or prismatic in shape. Preferably, the upper contact surface converges toward the lower contact surface at the front and back sides. The height of the cage can range from 6 mm to 15 mm along the central axis. The central cavity can have a volume ranging from 30 percent to 70 percent of the total volume of the body, preferably from 40 percent to 60 percent of the total volume of the body.

In one embodiment, the body has a first spring rate and is compressed along a central axis until the plurality of slots close to their respective minimal widths. Upon further compression, the body has a second spring rate that is 10 to 100 times greater than the first spring rate. In another embodiment, the second spring rate is 1 to 5 times greater than the first spring rate.

The plurality of slots extend through the circumferential sidewall preferably at a minimum of at least two different heights from the lower contact surface. In a preferred form of the invention, the plurality of slots include a first pair of slots at a first height from the lower contact surface and a second pair of slots at a second height from the lower contact surface, wherein the second height is greater than first height, and wherein the first pair of slots are staggered relative to the second pair of slots. A first pair of sectors remain between the first pair of slots and a second pair of sectors remain between the second pair of slots and result in an angular sum of at least 360°. In another embodiment, the sectors partially overlap each other and have an angular sum of greater than 360°. Preferably, each sector encloses an angle ranging from 450 to 150°. In a more preferred embodiment, each sector encloses an angle ranging from 90° to 120°.

BRIEF DESCRIPTION OF THE DRAWINGS

Further features and advantages of the invention can be ascertained from the following detailed description which is provided in connection with the attached drawings, wherein:

FIG. 2 illustrates a schematic representation of a strain regulation fusion cage according to the invention;

FIG. 3 illustrates a cross section of a schematic representation of a strain regulation fusion cage according to the invention shown in FIG. 2;

FIG. 4 illustrates another cross section of a schematic representation of a strain regulation fusion cage according to the invention shown in FIG. 2;

DETAILED DESCRIPTION OF THE INVENTION

The promotion of bone formation requires a certain strain level applied to graft material inside a fusion cage. The present invention advantageously allows the enclosed graft material in a fusion cage, implanted between two adjacent, opposing vertebrae, to be exposed to ideal strain levels. The fusion cage also protects the graft material from high strains that can lead to mechanical failure of the graft, thus applying consistent strain to the graft material irregardless of the applied physiological load.

Figure 1:
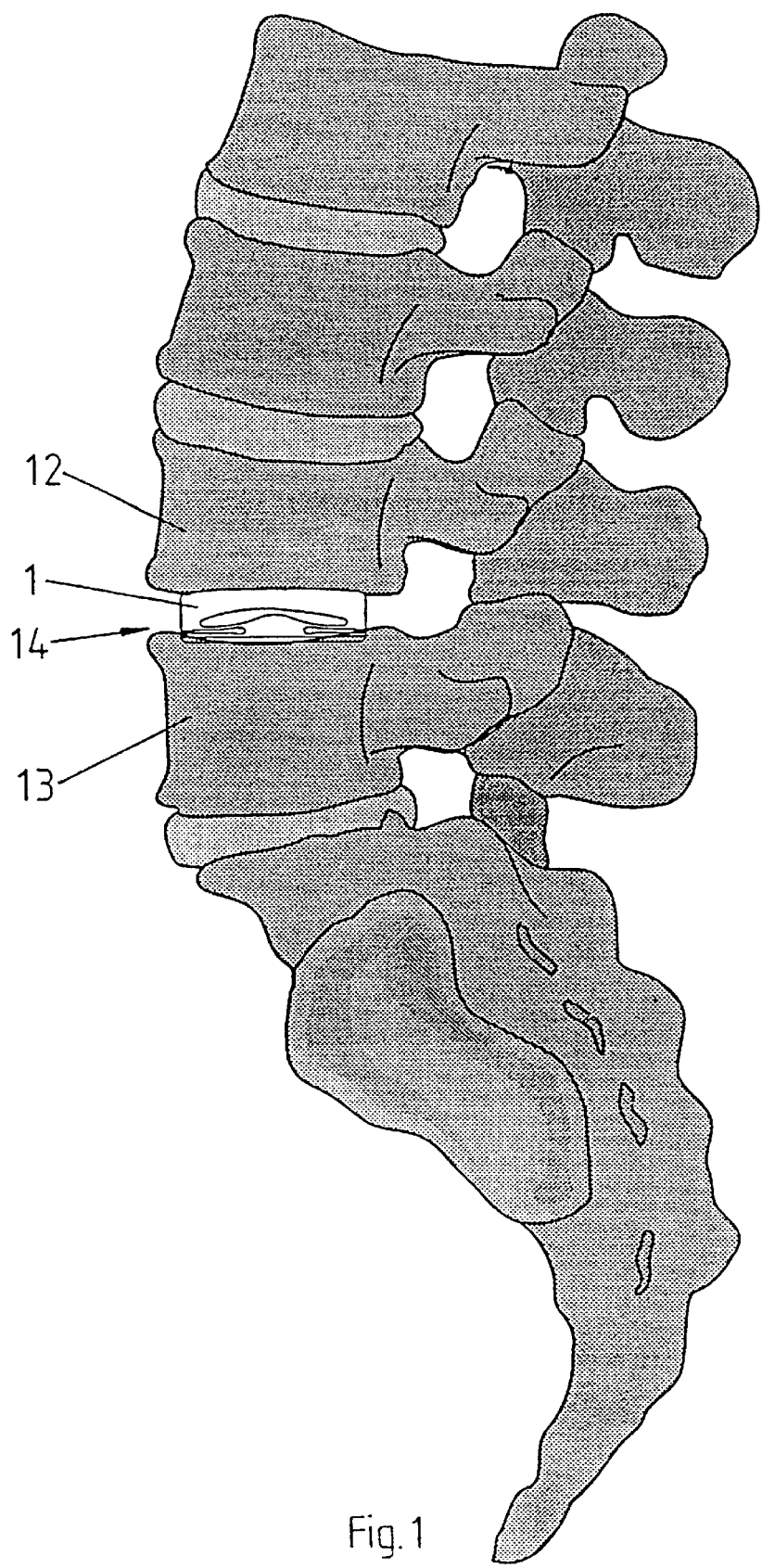
FIG. 1 illustrates a lateral view of a section of the vertebral column with an implanted strain regulating fusion cage according to one embodiment of the invention in a lumbar application.

FIG. 1 shows a lumbar application of a strain regulating fusion cage 1, according to one embodiment of the invention, implanted in an intervertebral space 14 between two vertebral bodies 12 and 13.

In FIG. 2, a schematic representation of a strain regulation fusion cage according to the invention is shown. The fusion cage 1 consists of a hollow cylinder with a central axis 2, an upper contact surface 3, a lower contact surface 4, and a coaxial cavity 5 extending between the upper contact surface 3 and the lower contact surface 4. At a height $H_1$, two sectorial slots 8 and 9 perforate the circumferential sidewall 10 symmetrical to a first diameter and from diametrical opposite directions, thus forming sectors 17 and 18 as shown in FIG. 4. Two additional sectorial slots 6 and 7 (slot 7 not shown in the FIG. 2) perforate the circumferential sidewall 10 at a height $H_2$, which is closer to the upper contact surface 3 than the height $H_1$. Slots 6 and 7, arranged at the upper height $H_2$, also perforate the circumferential sidewall 10 symmetrical to a second diameter and from diametrical opposite directions, thus forming sectors 15 and 16 as shown in FIG. 3. Slots 6 and 7 are staggered with slots 8 and 9, with the first diameter orthogonal to the second diameter. Furthermore, slots 6 and 7 and associated sectors 15 and 16, at the upper height $H_2$, partially overlap slots 8 and 9 and associated sectors 17 and 18, at the lower height $H_1$. The struts remaining (19, 20, 21, and 22) between slots 6, 7, 8, and 9 at the circumferential sidewall 10 may be elastically compressed when fusion cage 1 is compressed.

In one embodiment, the intervertebral cage is designed such that it permits the cage to be very compliant in the vertical direction until a certain displacement is reached. This displacement can be designed into the implant to allow the graft to be exposed to the desired level of strain of 1,000 $\mu\epsilon$ to 50,000 $\mu\epsilon$, preferably from 3,000 $\mu\epsilon$ to 10,000 $\mu\epsilon$.

Once this displacement has been reached, contact between the upper and lower portions of the cage is made and the cage becomes very stiff, permitting only very small amounts of additional strain for increased loads. This feature allows identical strains to be placed on the graft regardless of the applied load, e.g., 200 N or 1000 N.

Figure 5:
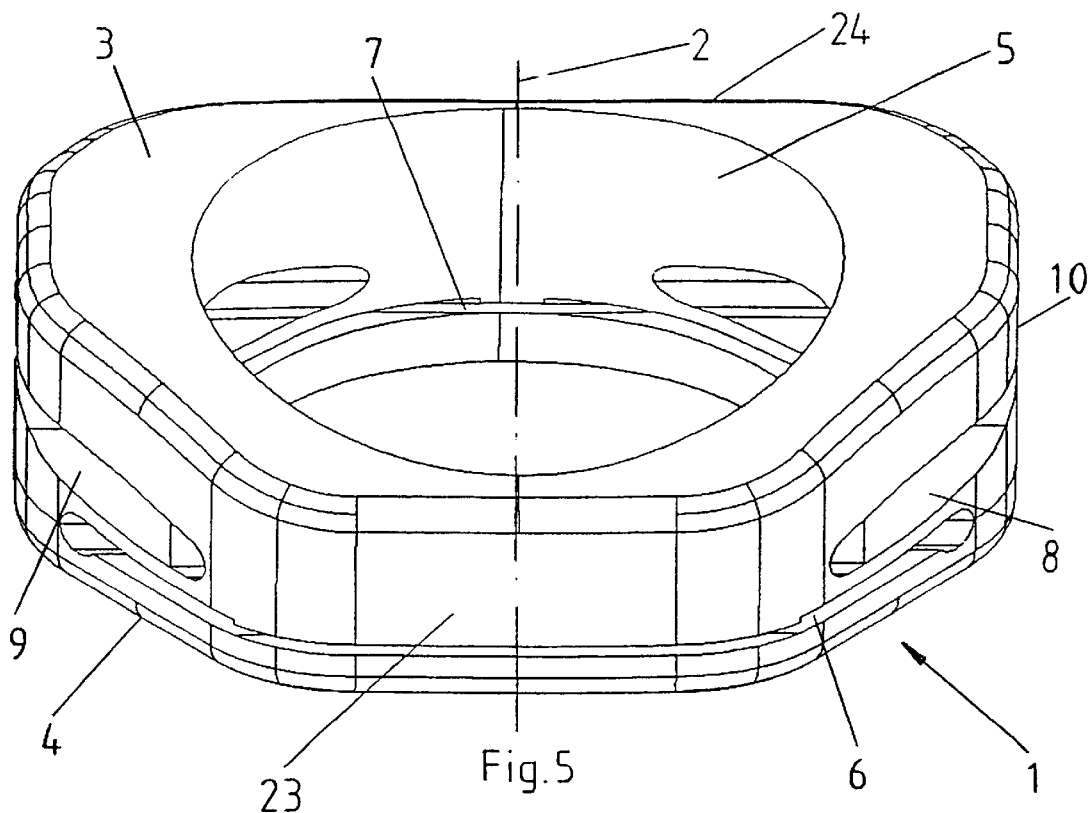
FIG. 5 illustrates a perspective view of a strain regulating fusion cage according to one embodiment of the invention.
Figure 6:
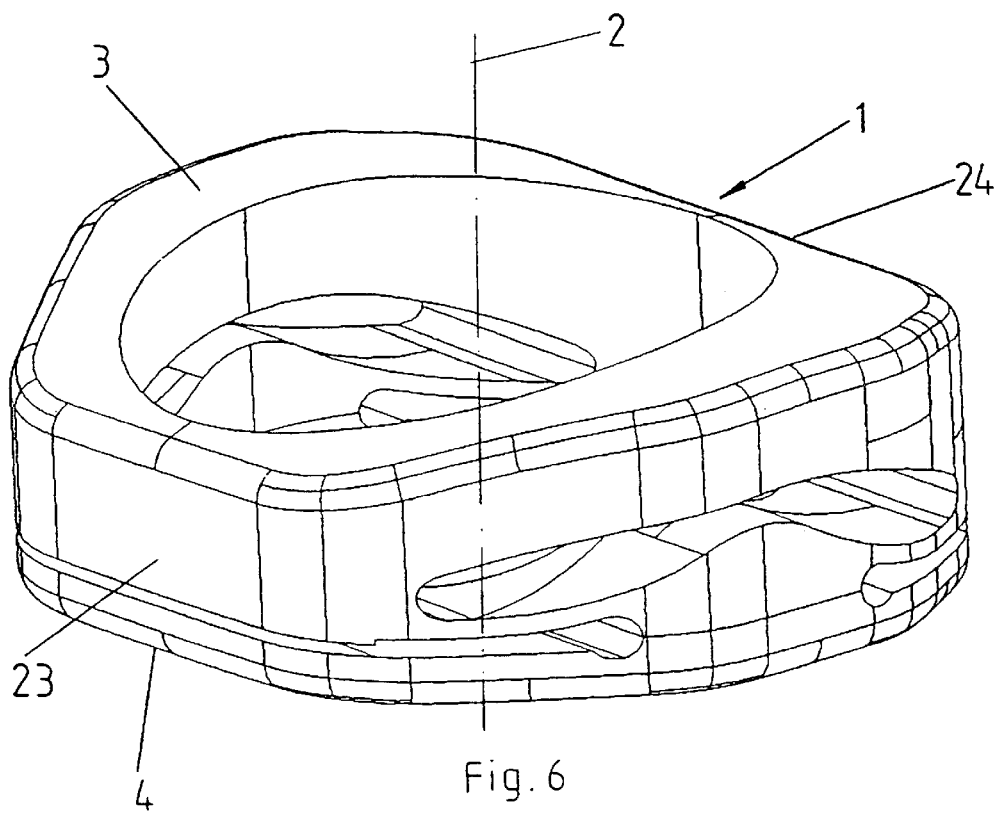
FIG. 6 illustrates another perspective view of a strain regulating fusion cage according to the embodiment of the invention shown in FIG. 5.

FIGS. 5 and 6 show a preferred embodiment of the strain regulation fusion cage 1 according to the invention. The fusion cage 1 has a prism-like exterior shape with a longitudinal axis 2, an upper contact surface 3 and a lower contact surface 4 transverse to its longitudinal axis, and a central cavity 5 for receiving bone graft material that is coaxial to the longitudinal axis 2 and extending between the upper contact surface 3 and the lower contact surface 4. The cross section perpendicular to the longitudinal axis 2 shows an exterior circumference of the fusion cage 1 that has the shape of an irregular polygon. The lower contact surface 4 is even and extends transversely to the longitudinal axis 2. Transverse to the front side 23 of the fusion cage 1, the upper contact surface 3 is convexly shaped and converges towards the lower contact surface 4 at the front side 23 and the back side 24. Parallel to the front side 23 of the fusion cage 1, the upper contact surface 3 is not curved so that the fusion cage 1 has a wedge-like shape. Slots 6, 7, 8, and 9 perforate the circumferential sidewall 10 of the fusion cage 1 at two planes transverse to the longitudinal axis 2, whereby the planes are situated at two different heights $H_1$ and $H_2$ above the lower contact surface 4. Each plane contains two slots 6, 7, 8, and 9 that are situated diametrically opposite within the circumferential sidewall 10. Slots 6 and 7, corresponding to height $H_1$, are closer to the lower contact surface 4 (FIG. 7) and run parallel to the front side 23 of the cage 1. In contrast, slots 8 and 9, corresponding to height $H_2$, are closer to the upper contact surface 3 (FIG. 7) and are orthogonal to the front side 23 of the fusion cage 1, so that the slots at each height cover opposite sectors of the circumferential sidewall 10. This arrangement is such that slots 6, 7, 8, and 9 are configured in a staggered design at the two different heights $H_1$ and $H_2$, and each slot 6, 7, 8, and 9 cover another sector of the circumferential sidewall 10. The slots (6, 7, 8, and 9) are arranged at the two different heights such that the angular sum of all the sectors amounts to at least 360°. In one embodiment, the slots at the two different heights partially overlap one another such that the angular sum of the all the sectors amounts to more than 360°.

Furthermore, slots 6 and 7, in the plane closer to the lower contact surface 4, are only partially parallel shaped. The parallel sections of slots 6 and 7 provide a minimal width $h_1$ and $h_2$ (FIG. 7) ranging from 0.018 mm to 0.15 mm, which upon compressing the body along the longitudinal axis 2 to the desired level of strain, the slots close elastically at their respective minimal widths $h_1$ and $h_2$ and significantly increase the stiffness of the cage 1. The nonparallel sections of slots 6 and 7 have a curved shape. Slots 8 and 9, in the plane corresponding to the greater height $H_2$, are shaped so that the curves form a small, almost line-like area with a minimal width $h_3$ and $h_4$. The minimal widths depend on the height of the implant and on the desired strain level.

In one exemplary embodiment, the height of the cage along the longitudinal axis amounts to 6 mm. The slots, in an unloaded state, have a width, measured in the direction of the longitudinal axis, of 0.018 mm. When the slots are closed under the required load, the resulting strain level amounts to 3,000 $\mu\epsilon$.

In another embodiment, the height of the cage along the central axis amounts to 15 mm and the slots, in an unloaded state, have a width of 0.15 mm. When the slots are closed under the applied load, the resulting strain level amounts to 10,000 $\mu\epsilon$.

Figure 7:
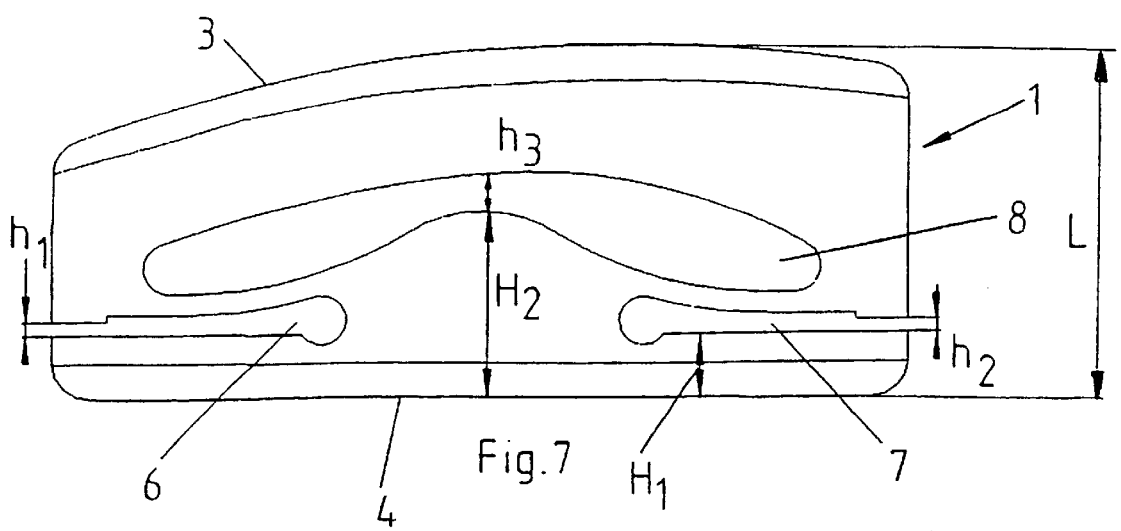
FIG. 7 illustrates a lateral view of a strain regulating fusion cage according to the embodiment of the invention shown in FIG. 5.
Figure 8:
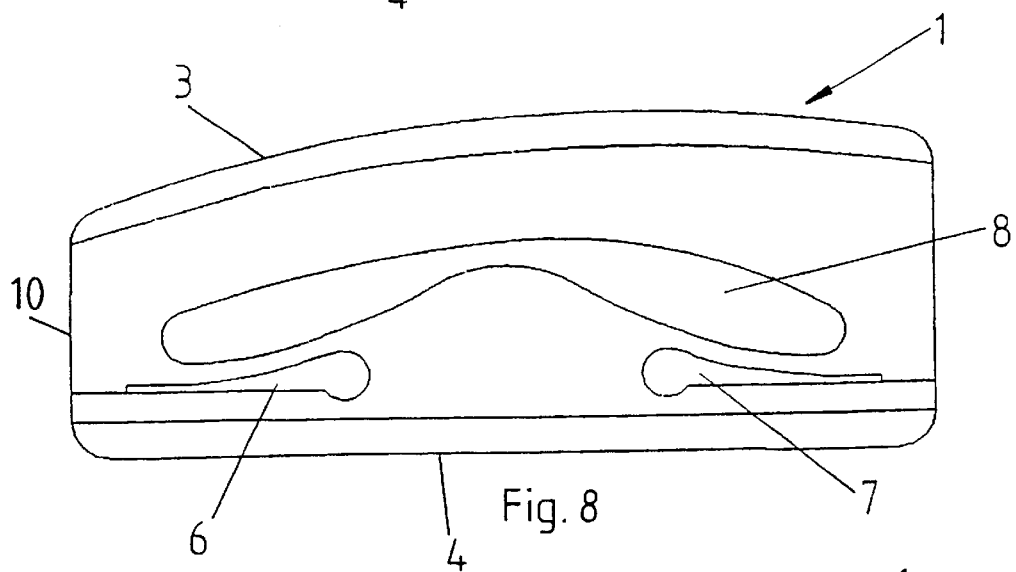
FIG. 8 illustrates a lateral view of a strain regulating fusion cage according to the embodiment of the invention shown in FIG. 5 with the lower slots are closed at their minimal widths.

FIG. 8 represents the fusion cage 1 illustrated in FIGS. 5, 6, and 7 whereby the fusion cage 1 is compressed so that slots 6 and 7, lying in the plane closer to the lower contact surface 4, are closed at the sections corresponding to a minimal widths $h_1$ and $h_2$.

Figure 9:
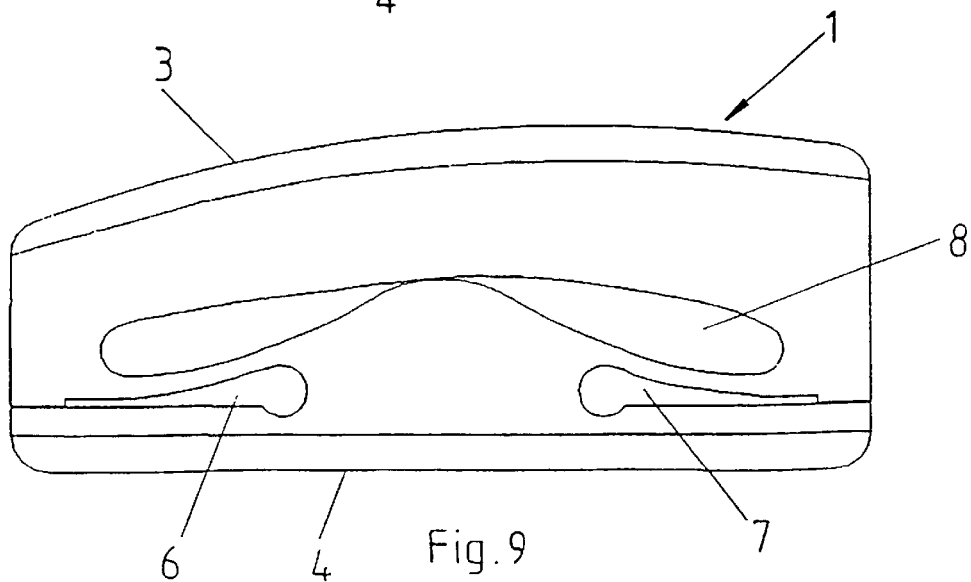
FIG. 9 illustrates a lateral view of a strain regulating fusion cage according to the embodiment of the invention shown in FIG. 5 with the lower and upper slots are closed at their minimal widths.

In FIG. 9, the fusion cage 1 as shown in FIGS. 5, 6, 7, and 8 is loaded so that the cage 1 is compressed so that slots 6 and 7, lying in the plane closer to the lower contact surface 4, and slots 8 and 9, lying in the plane closer to the upper contact surface 3, are closed at the sections corresponding to the minimal widths $h_1$, $h_2$, $h_3$, and $h_4$.

Figure 10:
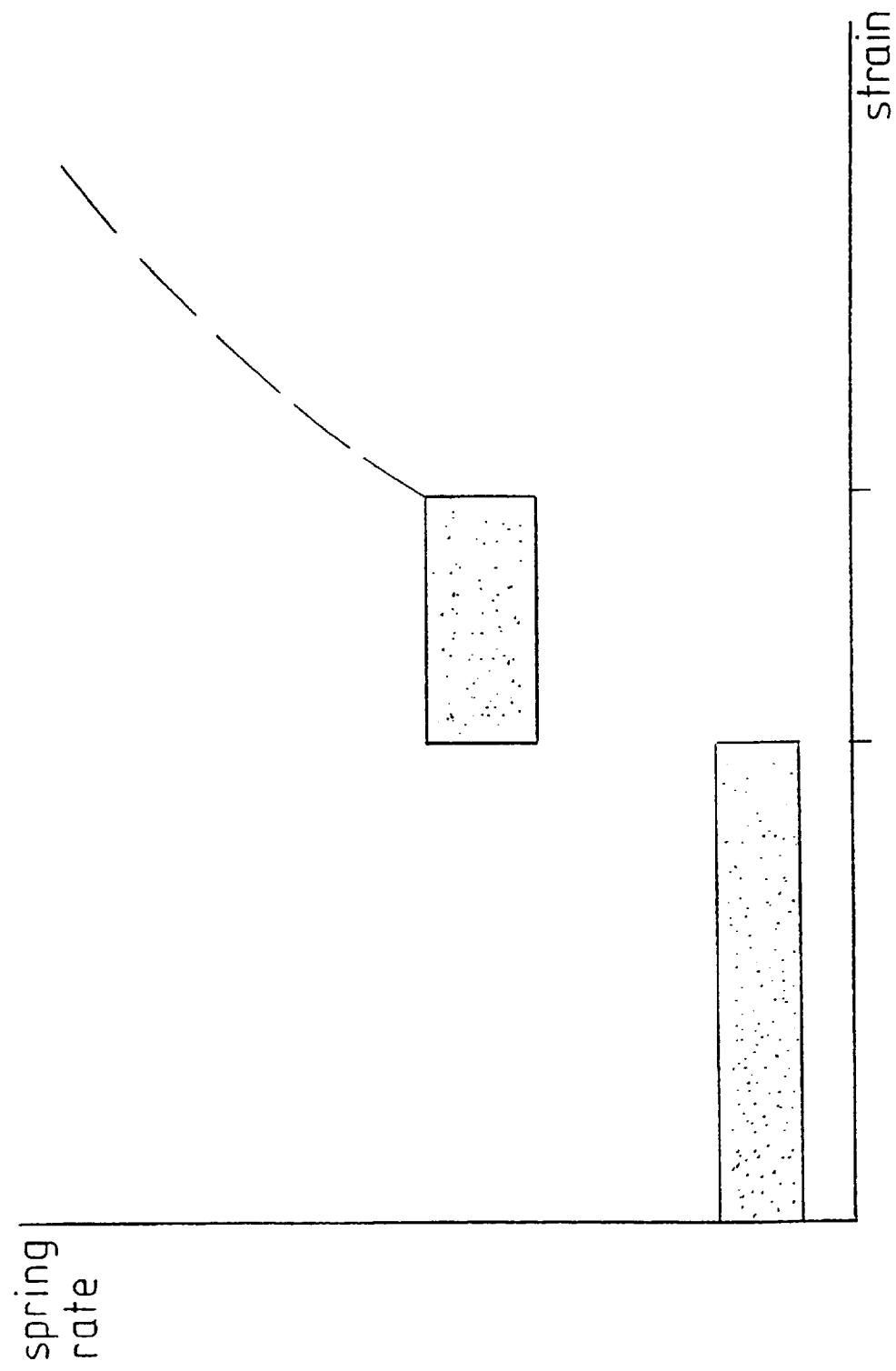
FIG. 10 illustrates a diagram representing the variable spring rate dependent of the strain applied to a strain regulating fusion cage according to the embodiment of the invention shown in FIG. 5.

FIG. 10 shows the spring rate of fusion cage 1 wherein the fusion cage coaxially provides a spring rate $c_1$ upon compression until slots 6 and 7 close at their minimal widths $h_1$ and $h_2$. Upon further compression, spring rate $c_2$ is achieved, which in one embodiment is 1 to 5 times greater than $c_1$, until slots 8 and 9 close at their minimal widths $h_3$ and $h_4$, thus causing a further increase of the fusion cage stiffness with an unknown gradient of the spring rate.

Figure 11:
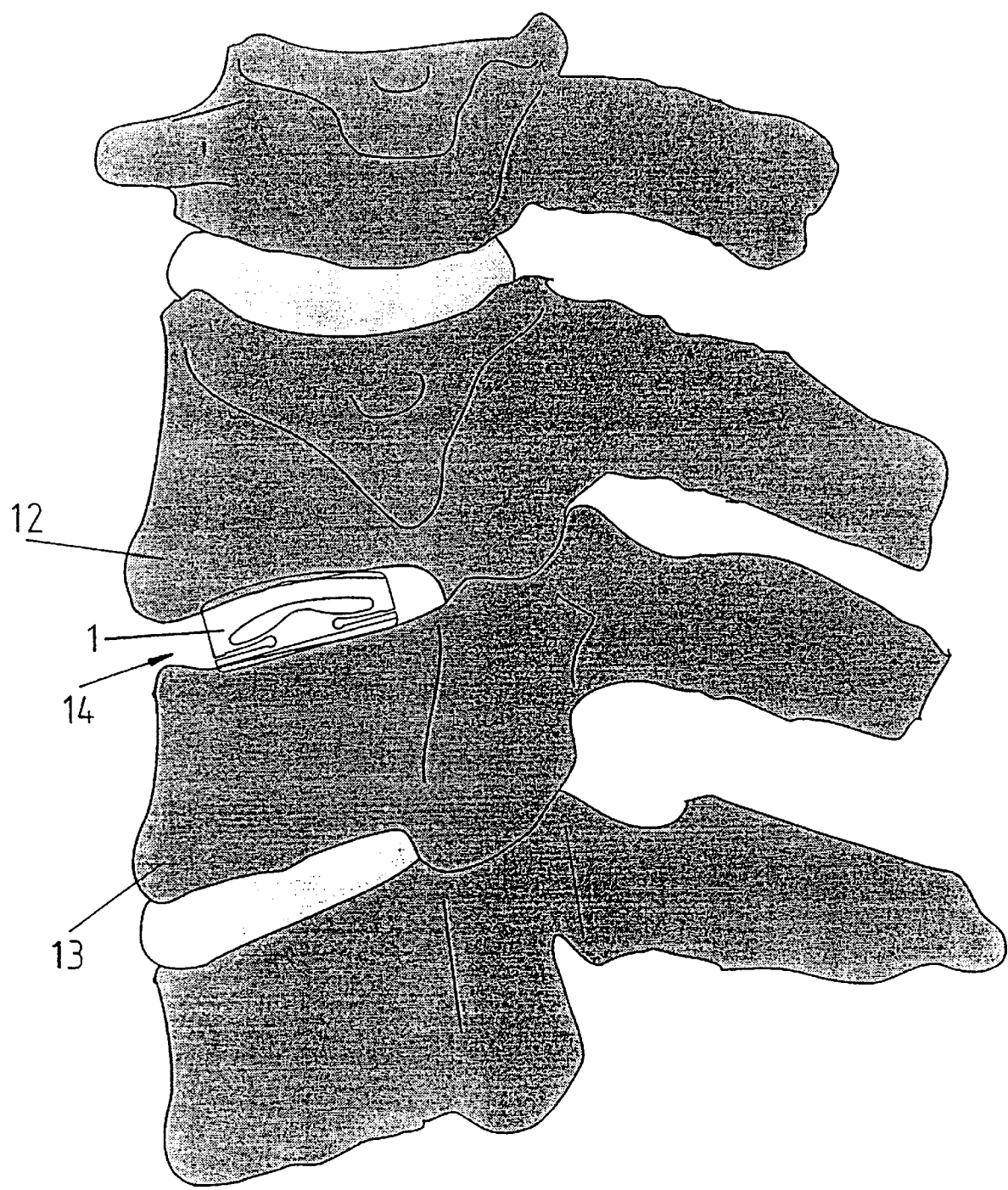
FIG. 11 illustrates a lateral view of a section of the vertebral column having a strain regulating fusion cage according to one embodiment of the invention implanted in an intervertebral space.

FIG. 11 shows fusion cage 1 implanted in an intervertebral space 14 between two vertebral bodies 12 and 13.

It is to be understood that the invention is not to be limited to the exact configuration as illustrated and described herein. For example, it should be apparent that a variety of materials would be suitable for use in the composition or method of making the fusion cage according to the Detailed Description of the Invention. Accordingly, all expedient modifications readily attainable by one of ordinary skill in the art from the disclosure set forth herein, or by routine experimentation therefrom, are deemed to be within the spirit and scope of the invention as defined by the appended claims.

What is claimed is:

1. An intervertebral fusion cage for implantation in an intervertebral space between adjacent vertebrae, comprising:
    a body having a central axis, a first outer surface, and a first stiffness;
    a central cavity for containing graft material having a second outer surface and extending through the body coaxial to the central axis;
    a circumferential sidewall between the first outer surface and the second outer surface;
    an upper and a lower contact surface perpendicular to the central axis, wherein the upper and lower contact surfaces contact the adjacent vertebrae; and
    a plurality of slots transverse to the central axis, each of the slots having a minimal width and extending through the circumferential sidewall, wherein upon compression of the body along the central axis, the slots close to their respective minimal widths providing the body a second stiffness greater than the first stiffness.

2. The cage of claim 1, wherein the body has a conical, cylindrical, or prismatic shape.

3. The cage of claim 1, wherein the upper contact surface has front and back sides, and wherein the upper contact surface converges toward the lower contact surface at the front and back sides.

4. The cage of claim 1, wherein the plurality of slots close to their respective minimal widths under a required load resulting in a strain level of 1,000 $\mu\epsilon$ to 50,000 $\mu\epsilon$.

5. The cage of claim 4, wherein the plurality of slots close to their respective minimal widths under a required load resulting in a strain level of 3,000 $\mu\epsilon$ to 10,000 $\mu\epsilon$.

6. The cage of claim 1, wherein the cage has a height ranging from 6 mm to 15 mm along the central axis.

7. The cage of claim 1, wherein the minimal widths range from 0.018 mm to 0.15 mm.

8. The cage of claim 1, wherein the body has a total volume and wherein the central cavity has a volume ranging from 30 percent to 70 percent of the total volume of the body.

9. The cage of claim 8, wherein the central cavity has a volume ranging from 40 percent to 60 percent of the total volume of the body.

10. The cage of claim 1, wherein the body has a first spring rate and is compressed along a central axis until the plurality of slots close to their respective minimal widths, and wherein upon further compression, the body has a second spring rate that is 10 to 100 times greater than the first spring rate.

11. The cage of claim 1, wherein the body has a first spring rate and is compressed along a central axis until the plurality of slots close to their respective minimal widths, and wherein upon further compression, the body has a second spring rate that is 1 to 5 times greater than the first spring rate.

12. The cage of claim 1, wherein the plurality of slots extend through the circumferential sidewall at a minimum of at least two different heights from the lower contact surface.

13. The cage of claim 12, wherein the plurality of slots comprise a first pair of slots at a first height from the lower contact surface and a second pair of slots at a second height from the lower contact surface, wherein the second height is greater than first height, and wherein the first pair of slots are staggered relative to the second pair of slots.

14. The cage of claim 13, wherein a first pair of sectors remain between the first pair of slots and a second pair of sectors remain between the second pair of slots.

15. The cage of claim 14, wherein an angular sum of the first pair of sectors and the second pair of sectors is at least 360°.

16. The cage of claim 15, wherein the first pair of sectors and the second pair of sectors partially overlap each other and have an angular sum of greater than 360°.

17. The cage of claim 14, wherein each sector in the first pair of sectors and the second pair of sectors encloses an angle ranging from 45° to 150°.

18. The cage of claim 17, wherein each sector in the first pair of sectors and the second pair of sectors encloses an angle ranging from 90° to 120°.

19. The cage of claim 1, wherein the minimal widths are different.

20. An intervertebral fusion cage for implantation in an intervertebral space between adjacent vertebrae, comprising:

a prismatic, conical, or cylindrical body comprising a central axis, a first outer surface, and a first stiffness;

a central cavity for containing graft material having a second outer surface and extending through the body coaxial to the central axis;

a circumferential sidewall between the first outer surface and the second outer surface;

an upper and a lower contact surface transverse to the central axis, wherein the upper and lower contact surfaces contact the adjacent vertebrae;

a first pair of slots at a first height from the lower contact surface transverse to the central axis and having a first minimal width extending through the circumferential sidewall; and a second pair of slots at a second height from the lower contact surface transverse to the central axis and having a second minimal width extending through the circumferential sidewall, wherein upon compression of the body along the central axis, the first pair of slots close to the first minimal width and the second pair of slots close to the second minimal width providing the body a second stiffness greater than the first stiffness.

21. An intervertebral fusion cage for implantation in an intervertebral space between adjacent vertebrae, comprising:

a prismatic body comprising a central axis, a first outer surface, and a first stiffness;

a central cavity for containing graft material having a second outer surface and extending through the body coaxial to the central axis;

a circumferential sidewall between the first outer surface and the second outer surface;

an upper and a lower contact surface transverse to the central axis, wherein the upper and lower contact surfaces contact the adjacent vertebrae;

a first pair of slots extending transversely through the sidewall at a first height from the lower contact surface, and each first pair of slots having a first cross-section taken transverse to each slot and in a plane parallel to the central axis, wherein the first cross-section includes a section with parallel walls and a section with curvilinear walls; and a second pair of slots extending transversely through the sidewall at a second height from the lower contact surface, and each second pair of slots having a second cross-section taken transverse to each slot and in a plane parallel to the central axis, wherein the second cross-section has substantially curvilinear walls, wherein upon compression of the body along the central axis, the first pair of slots compress and the parallel walls of the first cross-section close and the second pair of slots compress and only a portion of the curvilinear walls of the second cross-section close.

22. The cage of claim 21, wherein the upper contact surface has front and back sides, and wherein the upper contact surface converges toward the lower contact surface at the front and back sides.

23. The cage of claim 21, wherein the plurality of slots compress under a required load resulting in a strain level of 1,000 $\mu\epsilon$ to 50,000 $\mu\epsilon$.

24. The cage of claim 21, wherein the second height is greater than first height, and wherein the first pair of slots are staggered relative to the second pair of slots.

* * * * *